United States Patent [19]
Ardito

[11] Patent Number: 5,711,314
[45] Date of Patent: Jan. 27, 1998

[54] URINARY INCONTINENCE VALVE WITH DISTAL AND PROXIMAL ANCHORING MEANS

[75] Inventor: James R. Ardito, Coon Rapids, Minn.

[73] Assignee: PriMed International Corporation, Coon Rapids, Minn.

[21] Appl. No.: 746,429

[22] Filed: Nov. 8, 1996

[51] Int. Cl.$^6$ ........................................ A61F 5/48
[52] U.S. Cl. .......................... 128/885; 128/DIG. 25; 600/29
[58] Field of Search ..................... 128/846, 885, 128/DIG. 25; 600/29–31; 604/347–353, 330

[56] References Cited

U.S. PATENT DOCUMENTS

| | | | |
|---|---|---|---|
| 3,812,841 | 5/1974 | Isaacson | 128/DIG. 25 |
| 5,112,306 | 5/1992 | Burton | 128/DIG. 25 |
| 5,140,999 | 8/1992 | Ardito | 128/885 |
| 5,256,133 | 10/1993 | Spitz | 128/DIG. 25 |
| 5,513,659 | 5/1996 | Buuck | 128/885 |

*Primary Examiner*—Michael A. Brown
*Attorney, Agent, or Firm*—Haugen & Nikolai, PA

[57] ABSTRACT

The present invention is a urinary incontinence valve for positioning in a patient's urethra and bladder, and controlling the flow of urine therethrough. The valve includes an annular valve seat surface and a valve member cooperating with the valve seat surface for normally blocking urine flow. A compression spring normally urges valve member into sealing contact relative to the annular valve seat surface with a predetermined force. An actuator rod, supporting a first permanent magnet, is affixed to said valve and projects into the urinary bladder of the patient. A first anchoring mechanism comprises a deflectable spring mechanism which extends into the bladder and contacts an inner bladder surface adjacent an opening of the bladder into the urethra. A second anchoring mechanism comprising a retaining spring is positionable proximate the urethra meatus. The first and second anchoring mechanisms prevent migration of the urinary incontinence valve after it is properly positioned in the patient.

13 Claims, 6 Drawing Sheets

URINARY INCONTINENCE VALVE WITH DISTAL AND PROXIMAL ANCHORING MEANS

FIELD OF THE INVENTION

The present invention relates generally to medical devices and more particularly to an implantable, magnetically actuable valve mechanism which, when positioned in the urethra of a female patient, acts to selectively block urine flow, thus providing treatment for urinary incontinence.

BACKGROUND OF THE INVENTION

Urinary incontinence in both males and females remains a persistent problem, even though various methods and devices have been devised and proposed for treating the problem. For relatively short term situations, a catheter with its associated collection bag is well known. Long term indwelling catheters often lead to bladder infections because the catheter provides a rather direct passage into the bladder for bacteria and other microscopic organisms. Special waterproof, water retaining pants are also an option. However, patients shy away from their use due to embarrassment and potential odor problems.

One known approach in treating urinary incontinence involves the implantation of a valve in the urethra. Such a valve has a means operable external to the body to activate it from a closed, urine blocking position to an open, urine draining position. In this regard, reference is made to the Issacson U.S. Pat. No. 3,812,841 and the Bayer et al. U.S. Pat. No. 5,004,454. In each of these arrangements, the valve comprises a tubular body which may be inserted by an appropriate insertion stylet into the urethra. When a permanent magnet is brought into proximity with the implanted valve, but exterior to the body, the valve may be shifted from its closed position to its open position to allow the bladder to empty through the valve. Removal of the external magnet restores the valve to its closed urine-blocking position.

The prior art magnetically-actuable urinary incontinence valves described in the Issacson '841 patent and the Bayer et al. '454 patent have design defects which render them unsuitable for their intended purpose. In particular, in each of the designs, a tension type coil spring used to urge the valve against the valve seat. This spring is continuously exposed in the bladder and therefore, continuously bathed in urine. Pitting of the metal of the spring occurs and salt deposits build up on the spring element due to the continuous urine exposure and lead to valve failure. Moreover, in the event of spring failure, it is possible for parts of the valve assembly to snap loose and be projected with force into the bladder. The Bayer et al device is also deficient in that the valve orifice through which urine flows when the valve is actuated is quite small and the displacement of the valve surface from the valve seat is so small that the urine flow is reduced to a trickle at best. The valve displacement from its seat is restricted by the fact that the cone shaped valve member can only be displaced very slightly by the external magnet because its movement is constrained by the walls defining the bore of the valve body.

An improvement on the magnetically operated urinary incontinence valve can be found in U.S. Pat. No. 5,140,999 to Ardito. In this valve design, the valve is designed to fit into the neck of the bladder and included is an actuator rod which extends out of the valve body and into the bladder itself. This provided greater freedom of movement of a valve surface relative to the valve seat. A compression spring is disposed in the lumen of a valve body for urging the valve surface into sealing contact with its valve seat. Because the actuator rod extends exteriorly of the valve body and into the bladder, it is free to move a greater distance, providing greater displacement of the valve surface relative to its seat and permitting a more unrestricted flow of urine that can be achieved with other prior art devices, such as the Bayer '454 patent. Furthermore, the compression spring is not constantly exposed to urine and, hence, does not become encrusted with salt deposits or pitted.

While the Ardito '999 patent is advantageous over its prior art, one limitation is that it does not have an adequate anchoring mechanism to ensure that it cannot migrate in urethra. Therefore, what is needed is a urinary incontinence valve which is designed specifically for use with the female patient and which has provision for preventing unintentional displacement from the valve's working position.

SUMMARY OF THE INVENTION

The present invention is a urinary incontinence valve that includes a tubular housing containing a spring which normally holds a valve surface in contact with its valve seat to block the flow of urine through the valve and patient's urethra. The valve surface can be shifted to an open or urine passing position by approaching the implanted device with a permanent magnet. The valve returns to its closed, urine blocking position when the permanent magnet is removed.

The urinary incontinence valve of the present invention is locatable within the urethra of the patient in a location proximate the exit of the urethra from the bladder. It comprises a valve body having a proximal end and a distal end and an outer diameter sufficiently small to allow insertion of the valve assembly into the urethra of a patient. The valve body further includes a lumen extending longitudinally from the proximal end to its distal end through which urine can flow.

The device includes a distal anchoring mechanism which comprises a multi-lobe umbrella spring arrangement which is positionable in the bladder of the patient adjacent the opening of the bladder into the urethra. The umbrella springs are oriented generally transverse from the longitudinal axis of the valve body when unconstrained. When the valve is being inserted or removed, the umbrella springs will fold or deflect to be oriented substantially parallel to the longitudinal axis of the valve body. This first distal anchoring mechanism presents migration of the valve in the proximal direction.

A second anchoring mechanism is attachable to the proximal end of the valve body following the insertion thereof into the urethra and consists of a bow tie shaped retaining spring which when attached is positioned just proximate the urethral meatus. Like the umbrella spring arrangement, it is oriented generally transverse to the longitudinal axis of the valve body. The bow tie retaining spring is positioned on the proximal end of a retaining rod. The distal end of the retaining rod is threaded and mates with a threaded annular cap located on the proximal end of the valve body. These threaded annular cap also has a pull-ring member secured to its proximal end. The second anchoring mechanism prevents migration of the valve in the distal direction. The spacing between the multi-lobed umbrella spring and the bow tie spring can thus be adjusted to suit the anatomy of each patient.

A valve member is disposed in the lumen of the valve body proximate its distal end. The movable valve member has a valve surface cooperating with a valve seat. The valve member normally blocks liquid flow through the lumen of the tubular body. A compression spring is disposed in the lumen of the tubular body downstream of the valve seat for normally urging the valve surface into sealing contact with its seat. A valve stem is affixed to the valve member and projects outward of the lumen at the distal end of the valve body. The valve stem is provided with a magnetizable member on its distal end. When a permanent magnet is brought into the proximity of the magnetizable member on the valve stem, the valve is tipped open relative to its seat, allowing release and flow of urine through the valve body. Because the valve stem extends from the valve body and into the bladder, it is free to move a greater distance, thus providing greater displacement of the valve surface relative to its seat and permitting a more unrestrictive flow of urine.

The force with which the valve surface is pressed against the valve seat is readily adjustable by a means of the threaded annular cap secured to the proximal end of the valve body and on which the compression spring is seated. This allows the valve to remain closed until actuated by a permanent magnet or until the head of the urine within the bladder exerts a sufficient force on the valve to overcome the spring force and allow some limited drainage of the bladder even without the use of the external permanent magnet. This prevents back-up of urine into the ureters and potential kidney damage.

A tubular member with an inner sleeve is used for inserting the incontinence valve. This tubular member has an inner diameter slightly larger than the outer diameter of the incontinence valve. The incontinence valve, without the retaining post and bow tie spring arrangement, is inserted into the tubular member. As the valve is inserted into the tubular member, the umbrella springs are deflected to a portion generally parallel to the longitudinal axis of the valve body. The tubular member containing valve is then inserted into the urethra and a portion extends into the bladder. The inner sleeve of the tubular member is then used to push the valve out of the tubular member.

As the valve is pushed out of the tubular member, the umbrella springs deploy and retain their generally transverse orientation once into the bladder and out of the confines of the tubular member. After the springs have been deployed, the tubular member is removed. The pull-ring extending from the proximal end of the valve body is grasped by a suitable hook instrument and the valve is pulled down until the umbrella springs are properly seated against the bladder walls adjacent the opening into the urethra. The lower anchoring retaining spring is then positioned by inserting the threaded retaining rod into the annular cap and adjusting it for a proper fit.

When the valve is to be removed from the patient, the tubular member is inserted into the urethra surrounding the valve. The ring secured to the annular cap is grasped and the valve is pulled out through the tubular member, with the umbrella springs deflecting to a position parallel to the longitudinal axis of the valve body as they contact the interior of the tubular member. Once the valve is removed, the tubular member can then be removed.

DESCRIPTION OF THE DRAWINGS

The foregoing features and advantages of the invention will become apparent to those skilled in the art from the following detailed description of the preferred embodiment, especially when considered in conjunction with the accompany drawings in which.

DETAILED DESCRIPTION OF THE PREFERRED EMBODIMENT

Figure 1:
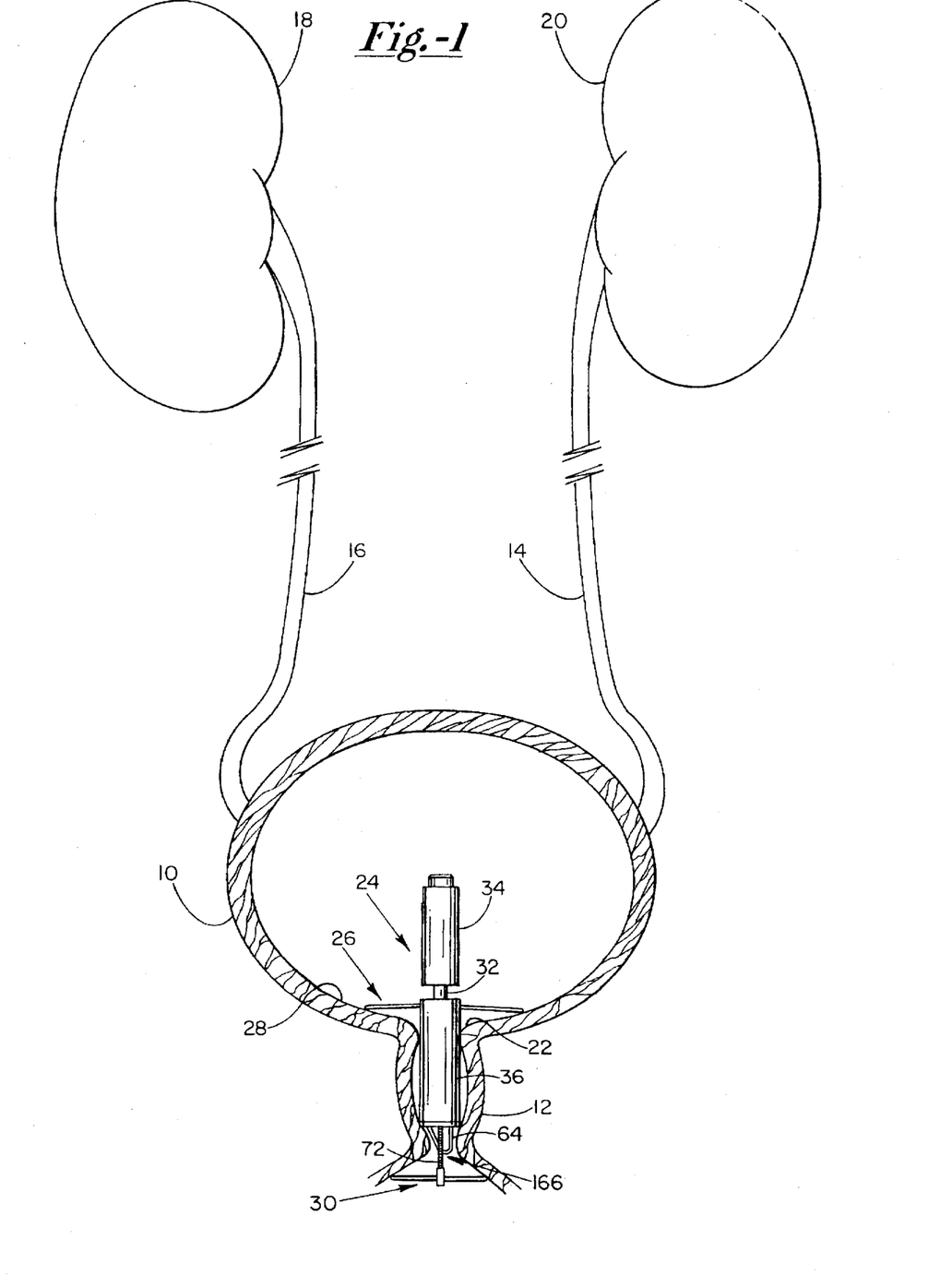
FIG. 1 is a cross-sectional view taken through the bladder and urethra of a female patient and showing the placement of the urinary incontinence valve of the present invention.
Figure 2:
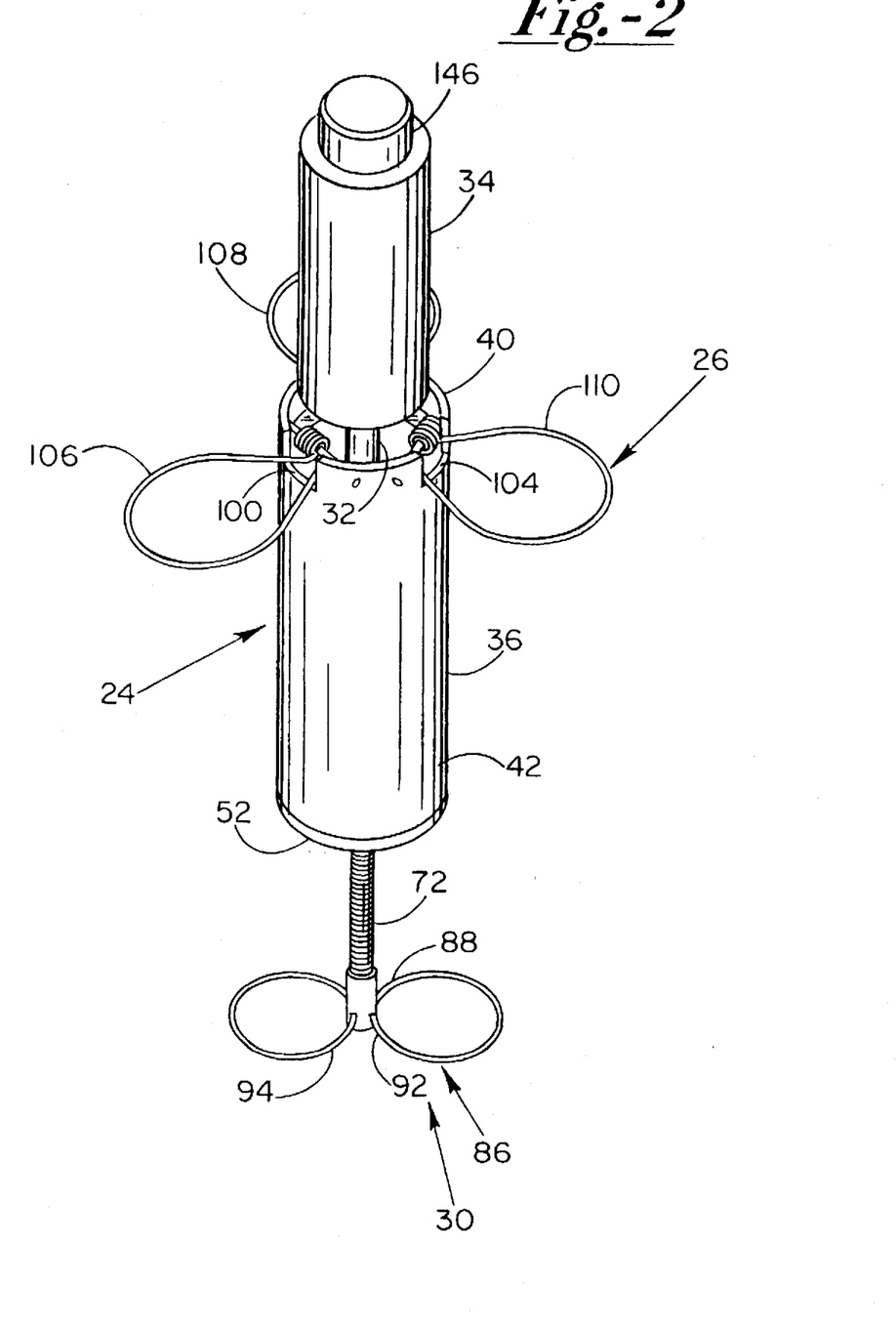
FIG. 2 is an enlarged perspective view of the preferred embodiment of the urinary incontinence valve of the present invention.

Referring to FIG. 1, there is shown a cross-sectional view taken through the urinary bladder 10 and urethra 12 of a female patient. Tubular organs 14 and 16 are the right and left ureters that carry urine from the kidneys 18 and 20 into the interior of the bladder 10. A smooth muscle called the internal urethral sphincter surrounds the opening 22 of the bladder into the urethra 12. Due to trauma or disease, the sphincter may lose its ability to constrict and release, leading to urinary incontinence, i.e., the uncontrolled flow of urine from the bladder through the urethra.

The urinary incontinence valve 24 of the present invention is shown positioned within the urethra and is designated number 24. It is positioned in the area surrounded by the external sphincter. A distal anchoring spring arrangement 26 associated with the valve 24 extends into the bladder 10 and contacts the inner wall 28 of surrounding the opening 22 into the urethra 12. A proximal anchoring spring arrangement 30, also associated with the valve 24, extends from the valve 24 to the meatus of the urethra 12. A valve stem 32 extends out of the distal end of the valve body 35 of valve 24 and into the interior of bladder 10. A magnetizable member 34 is affixed to the distal end of the valve stem 32. This member 34 is preferably a rare earth magnet hermetically sealed in a stainless steel gold plated can which is inert to body fluids, especially urine.

Figure 3:
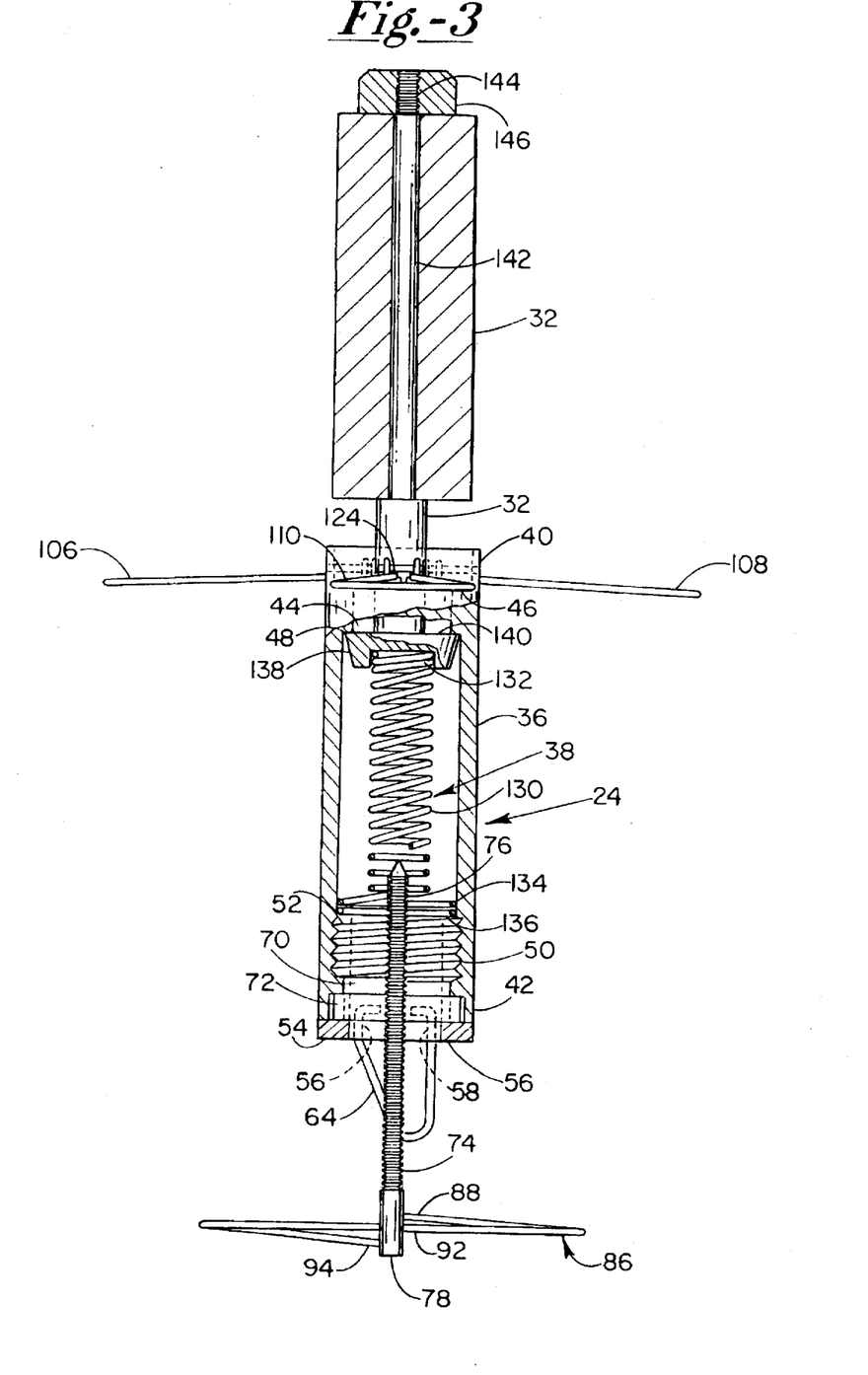
FIG. 3 is a greatly enlarged longitudinal cross-sectional view taken through the urinary incontinence valve of FIG. 2.

As seen in FIG. 3, the valve body 36 has a lumen 38 extending from a distal end 40 to a proximal end 42. The lumen 38 includes a narrow portion 44 approximate the distal end 40. The change in diameter at the narrow portion 44 forms a first annular internal ledge 46 and a second annular internal ledge 48. The proximal anchoring arrangement 30 and the distal anchoring mechanism 26 will now be described.

Figures 4, 8:
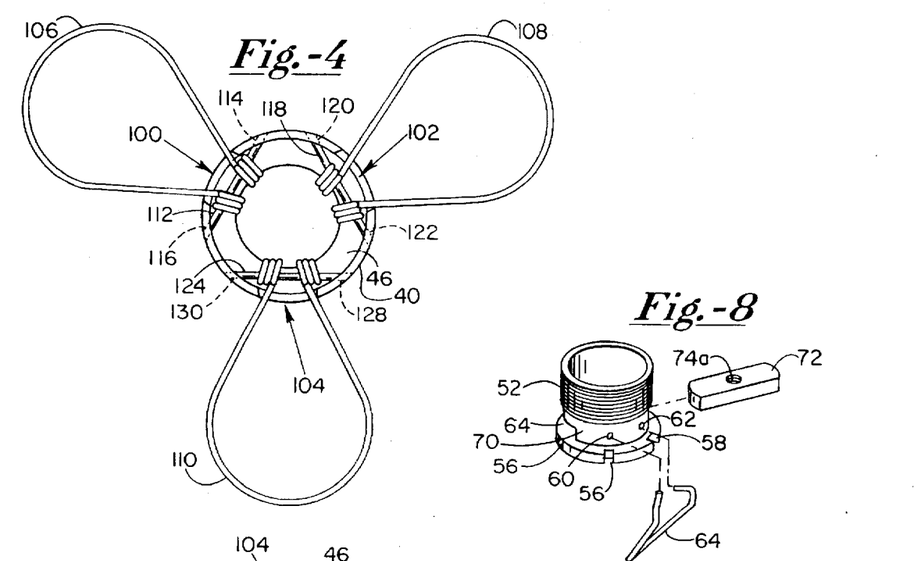
FIG. 4 is an enlarged top plan view of the valve body of the present invention showing the umbrella retention spring.
FIG. 8 is an exploded perspective view of the annular cap portion of the present invention.

An annular base cap 54 (FIG. 3) is fit into lumen 38 at the proximal end 42 of the valve body. The annular base cap 54 includes the threaded annular portion 52 and an annular plate 56 with a central opening through which urine will flow as will be explained later. The threaded annular member 52 mates with the interior threaded portion 50 of the lumen as seen in FIG. 3. Turning now to FIG. 8, the annular plate 56 include two slots 57 and 58 and two apertures 60 and 62, one associated with each slot. A pull-ring 64 fits into the slots 57 and 58 with its ends positioned in the apertures 60 and 62 for a secure fit as seen in FIG. 3.

The annular base cap 54 also includes two opposing slots 64 and 66, an annular wall 70 extending between the threaded portion 52 and the annular plate 56. A retaining bar 70 fits into the slots 64 and 66 and extends across the diameter of the annular plate. The retaining bar 72 includes an aperture 74a through which a retaining post 74 is threaded. The distal end 76 of the retaining post 74 extends into the lumen 38 of the valve body 36. The threaded configuration allows the physician to adjust the length of the retaining post 74 that extends from the proximal end 42 valve body 36 to comfortably fit the valve assembly 24 to each individual patient.

The proximal end 78 of retaining post 74 extends from the proximal end 42 of the valve body 36 and is not threaded. The proximal end 42 has three retaining post holes 80, 82 and 84 shown in hidden lines in FIGS. 6 and 7. The retaining spring 86 is secured to the retaining post 72 via these post holes 80, 82 and 84.

Figures 5, 6, 7:
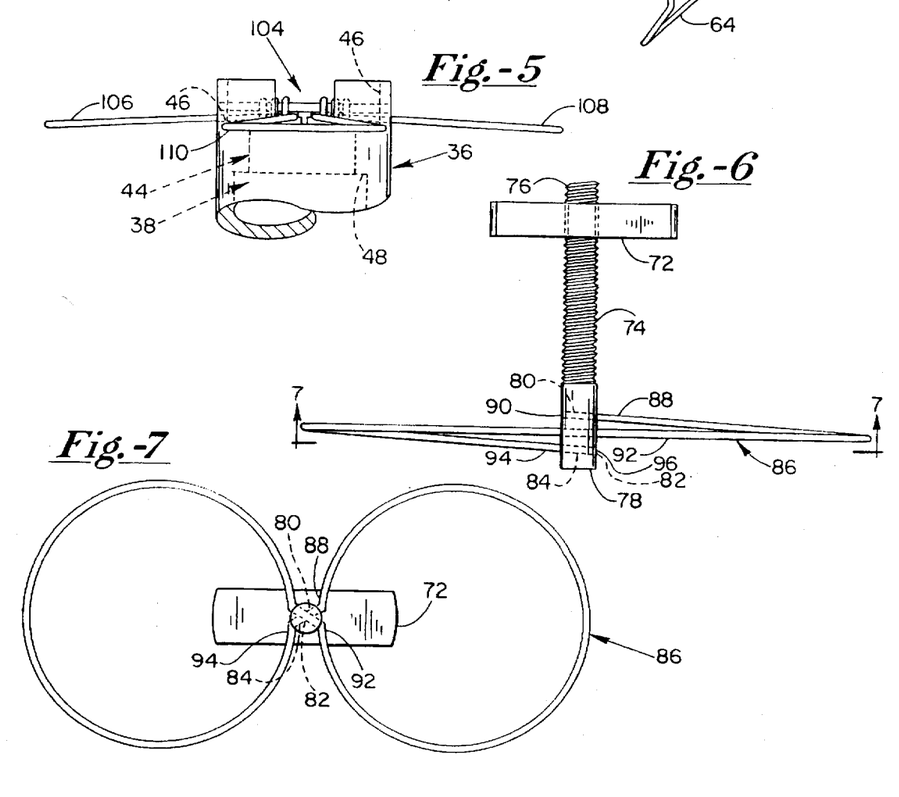
FIG. 5 is a detail side view of the upper portion of the valve body of the present invention.
FIG. 6 is an enlarged side view of the bow-tie retaining spring and retaining post of the present invention.
FIG. 7 is an enlarged bottom plan view of the bow-tie retaining spring and retaining post of the present invention.
Figure 9:
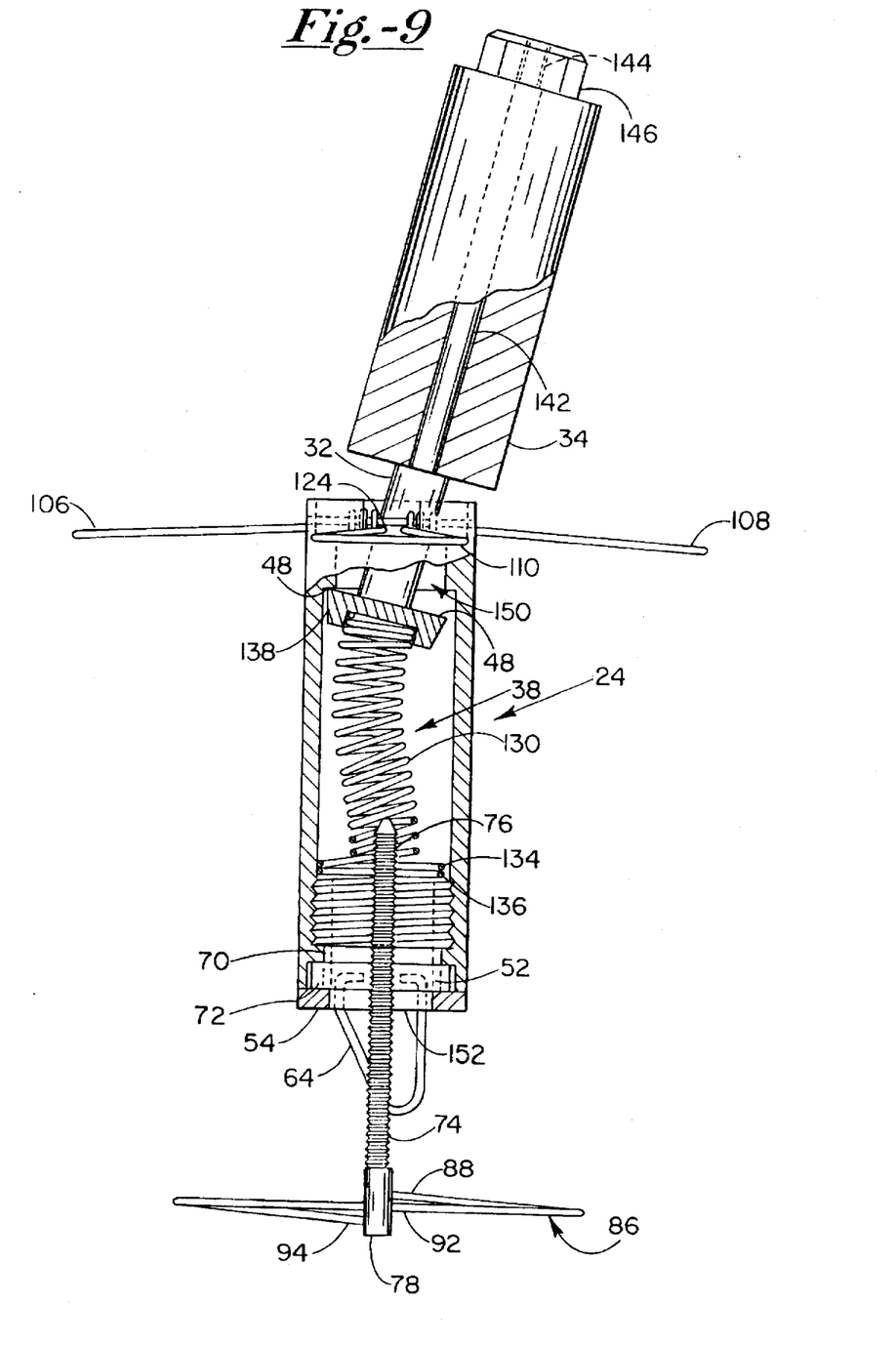
FIG. 9 is a longitudinal cross-sectional view taken through the urinary incontinence valve of FIG. 2 showing the valve in the open position.

As seen in FIGS. 6 and 7, the retaining spring 86 resembles a bow tie configuration with the retaining post 74 positioned in its center. A first end 88 of the retaining spring 86 is inserted into post hole 80 and is ground flush with the post surface and spot welded at 90. The intermediate portion 92 of the spring extends through the center post hole 82. The second end 94 of the retaining spring 86 is inserted into the third post hole 84. Like the first end 88, it is ground flush with the post surface and spot welded in place at 96.

The distal anchoring arrangement 26 is located on the distal end 40 of the valve body 36 as shown in FIGS. 1, 2, 3, 4 and 5. Three slots 100, 102 and 104 are evenly radially spaced around the upper edge of the valve body 36 for receiving one of three umbrella springs, designated 106, 108 and 110. The slots 100, 102 and 104 end approximate the annular ledge 46 formed in lumen 38. Umbrella spring 106 is mounted to the valve body 36 via a spring shaft 112. The spring shaft enters holes 114 and 116 formed in the valve body 36 on either side of slot 100. The ends of the shaft are ground flush with the outside surface of valve body 36 and spot welded on the interior of the valve body 36. Likewise, umbrella spring 108 is mounted to the valve body 36 via a spring shaft 118. This spring shaft is inserted into holes 120 and 122 formed on either side of slot 102 and ground flush with the outside wall of valve body 36 and spot welded on the interior of the valve body 36. Lastly, umbrella spring 110 is mounted via spring shaft 124 which in turn is inserted into holes 126 and 128 located on either side of slot 104. The ends of shaft 124 are also ground flush with the outside wall of the valve body 36 and spot welded on the interior of the valve body 36.

Each spring is preferably made of 316 stainless steel with gold plating wire having a diameter of 0.012 inches. The lobe formed is preferably 0.5 inches long and approximately 0.350 inches at its widest portion. it is wrapped sufficiently around its spring shaft so that it firmly holds its unrestrained position.

The multi-lobe umbrella springs 106, 108 and 110 are oriented in a direction generally transverse to the longitudinal axis of the valve body 36 when in their unconstrained positions. The umbrella springs 106, 108 and 110 fold about their respective spring shafts 112, 118 and 124. This enables the umbrella springs to deflect to a position generally parallel with the longitudinal axis of the valve body 36 to enable the valve 24 to be inserted and removed without damaging the urethra or opening into the bladder 10 as will be described later.

Turning now to FIG. 3, the internal valve arrangement will be described. A compression spring 130 is positioned within the lumen 38 of the valve and has a distal end 132 and a proximal end 134. The spring 130 is seated in the distal end 136 of annular base cap 54. The spring's distal end 130 fits into a cylindrical cavity formed in a valve member 138 having a valve surface 140. Spring 130 normally urges the valve surface 140 into a sealing relationship with respect to the valve seat formed by the annular ledge 48. The valve member 138 is fixed to the valve stem 32 that extends from the distal end 40 of valve body 36. The valve member 138 fits against the annular ledge 48 forming a water tight seal.

The force with which the valve surface 140 is pressed against the valve seat 48 is readily adjustable by a means of the threaded annular cap 54 on which the compression spring 130 is seated. This allows the valve to remain closed until actuated by a permanent magnet or until the head of the urine within the bladder exerts a sufficient force on the valve to overcome the spring force and allow some limited drainage of the bladder even without the use of the external permanent magnet. This prevents back-up of urine into the ureters and potential kidney damage.

Magnetizable member 34 has a bore 142 which receives the valve stem 32 therethrough. A threaded portion 144 of the stem rod 142 extends from the magnetizable member 34 and receives a stem nut 146 securing the magnetizable member 34 to the valve stem 32. The valve stem 32 positions the magnetizable member 34 into the bladder 10 when the valve body 36 is positioned within the confines of the external sphincter muscle as shown in FIG. 1. By bringing a permanent magnet sufficiently close to the magnetizable member 34, it will be attracted to the magnet and will cause the valve member 138 to tip as shown in FIG. 8. This allows urine to flow through the opening 150 formed through the lumen 38, through the central opening 152 of the annular cap 54 and then out the urethra 12. Also, as described above, if the force of the urine on the valve member 138 exerts a sufficient force to overcome the force of compression spring 130, the valve member 138 will tip slightly to allow drainage of urine.

When the permanent magnet is removed, the spring 130 will restore the valve member 138 to its sealed position relative to the valve seat formed by annular ledge 48. Likewise, in the event the valve member 138 was tipped due to the amount of the urine in the bladder, once a sufficient amount of urine has drained from the bladder. the compression spring force will overcome the force of the urine and will urge the valve member 138 back into a sealing relationship with the valve seat 48.

Figure 10:
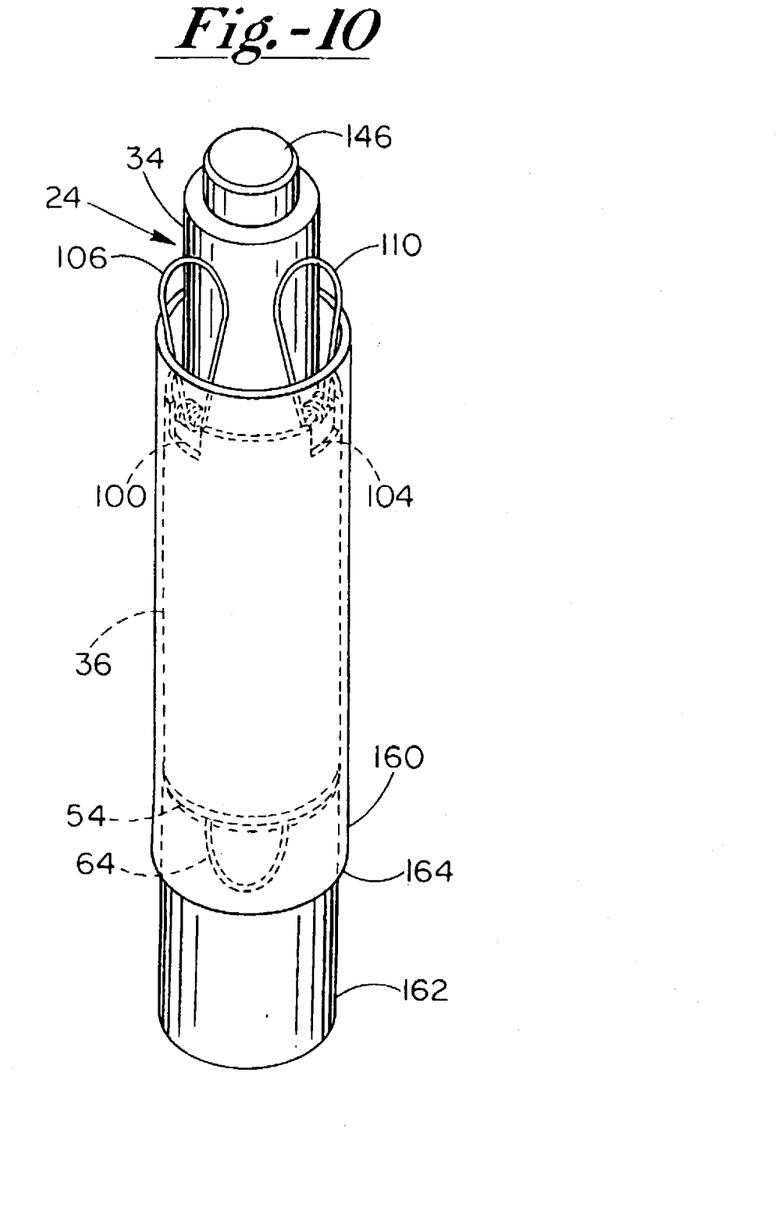
FIG. 10 is a perspective view showing a tubular insertion member surrounding the valve facilitating the inserting and positioning of the valve in the urethra.

The valve body is positioned in the urethra through use of a tubular insertion tool member 160 shown in FIG. 10. The tubular insertion tool member 160 is sized to extend through the urethra 12 and into the opening 22 of the bladder 10. The tool member 160 has an inner diameter slightly larger than the outer diameter of the incontinence valve 24. The tool member 160 further includes a sleeve 162 that fits within the inner diameter of the tool member 160 from end 164. The valve 24 is inserted into the tool member 160 from end 166. As it slides into the tool member 160, the umbrella springs 106, 108 and 110 deflect about their respective spring shafts 112, 118 and 124 and become oriented in a direction generally parallel to the longitudinal axis of the valve body 36, as seen in FIG. 10.

The incontinence valve is then positioned inserting the tool member 160 into the urethra 12. The inner sleeve 162 is then pushed into the tool member 160, pushing a portion of the incontinence valve into the bladder 10. As the upper end of valve 24 exits the tool member 160, the umbrella springs 106, 108 and 110 deploy. The tool member 160 is then withdrawn from the urethra 112. The physician grasps ring 64 to pull on the valve to insure it is firmly seated with the umbrella springs 106, 108 and 110 contacting the inside bladder wall adjacent the opening 122 into the urethra 12.

Once the valve 24 is in position, the physician then inserts the retaining post 74 into the retaining pin 72 and adjusts the amount of the post 74 extending from the proximal end 42 of the valve body 36. The length must be adjusted such that the retaining spring 86 contacts the patient in the tissue surrounding the meatus 166 of the urethra 12 as seen in FIG. 1.

The valve 24 is held in place and prevented from migrating in the proximal direction by the umbrella springs 106, 108 and 110 in the bladder 10 which rest on the wall of the bladder surrounding the opening 22 of the bladder into the urethra 12. Likewise, the bow-tie retaining spring 86 is positioned against the patient's skin adjacent the meatus 166 of the urethra 12 and assists in holding the valve 24 in place and preventing migration of the valve in the distal direction. The position of the bow-tie retaining spring 86 with respect to the patient's body is adjusted by rotating the retaining post 74 in the desired direction to lengthen or shorten the length of the retaining post 74 extending from the valve body 36.

When it is desired to remove the valve 24, the retaining post 74 and bow-tie spring are removed and the tool member 160 is inserted into the urethra surrounding the valve 24. The retaining ring 64 is then grasped with an approximate and pulled proximally. As the valve 24 is pulled through the tool member 160, the umbrella springs 106, 108 and 110 deflect such that they will pivot about their respective spring pins to a position generally parallel to the longitudinal axis of the valve body. The valve 24 is thus removed without damage to the bladder opening 22 or urethra 12. Once the valve 24 is removed, the tool member 160 is removed.

The valve 24, including the proximal anchoring means 30 and distal anchoring means 26, is preferably formed from stainless steel, but may be formed from any member of the suitable medical grade plastic material. When formed from stainless steel, it has been found desirable to coat the exterior with gold or coat it with a layer of a suitable elastomeric material such as silicon rubber. It has also been found expedient to coat lumen 38 of the valve body 36 with a film of a suitable polymeric material such as polytetrafluroethylene (Teflon).

This invention has been described herein in considerable detail in order to comply with the patent statutes and to provide those skilled in the art with the information needed to apply the novel principals and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed:

1. A urinary incontinence valve disposable in the urethra in a patient for controlling the flow of urine therethrough comprising:
    (a) a tubular member having a proximal end and an distal end and a lumen extending longitudinally from said proximal end to said distal end through which urine can flow;
    (b) a valve mechanism in said tubular body for selectively allowing passage of urine through said lumen;
    (c) a first anchoring mechanism affixed proximate said distal end of said tubular body; and
    (d) a second anchoring mechanism selectively positioned on said proximal end of said tubular body whereby said second anchoring mechanism is selectively positioned to custom-fit said valve for said patient, wherein said first anchoring means includes a deployable mechanism affixed to said tubular body proximate its distal end.

2. An urinary incontinence valve of claim 1 wherein said first anchoring mechanism includes a deployable umbrella spring mechanism positionable within the bladder of the patient adjacent the opening of the bladder into the urethra.

3. The urinary incontinence valve of claim 1 wherein said second anchoring mechanism includes a stop member selectively positionable proximate the meatus of the urethra.

4. A urinary incontinence valve of claim 1 and further including a tubular member surrounding said tubular body and said first anchoring mechanism for insertion and removal of said urinary incontinence valve into said urethra.

5. A urinary incontinence valve disposable in the urethra in a patient for controlling the flow of urine therethrough comprising:
    (a) a tubular member having a proximal end and an distal end and a lumen extending longitudinally from said proximal end to said distal end through which urine can flow;
    (b) a valve mechanism in said tubular body for selectively allowing passage of urine through said lumen;
    (c) a first anchoring mechanism affixed proximate said distal end of said tubular body, said first anchoring mechanism includes a deployable umbrella spring mechanism positionable within the bladder of the patient adjacent the opening of the bladder into the urethra, said umbrella spring mechanism is selectively movable between a first position extending generally transverse to a longitudinal axis of said tubular body and a second position generally parallel to said longitudinal axis of said tubular body; and
    (d) a second anchoring mechanism selectively positioned on said proximal end of said tubular body whereby said second anchoring mechanism is selectively positioned to custom-fit said valve for said patient.

6. A urinary incontinence valve disposable in the urethra in a patient for controlling the flow of urine therethrough comprising:
    (a) a tubular member having a proximal end and an distal end and a lumen extending longitudinally from said proximal end to said distal end through which urine can flow;
    (b) a valve mechanism in said tubular body for selectively allowing passage of urine through said lumen;
    (c) a first anchoring mechanism affixed proximate said distal end of said tubular body; and
    (d) a second anchoring mechanism selectively coupled to said proximal end of said tubular body, wherein the urinary incontinence valve is made of stainless steel and includes a gold plating on the exterior surface thereof and a compatible polymeric film coating on a wall surface defining said lumen.

7. A urinary incontinence valve for positioning in a patient's urethra and bladder and controlling the flow of urine therethrough, comprising:

(a) a tubular body having a proximal end, a distal end and an outer diameter sufficiently small to allow insertion into the urethra of the patient and a lumen extending longitudinally from said proximate end to said distal end through which urine can flow;

(b) a generally planar annular valve seat surface disposed in said lumen of said tubular body proximate said distal end;

(c) a valve member having a greater planar valve surface cooperating with said planar valve seat surface for normally blocking urine flow through said lumen;

(d) an actuator rod affixed to said valve member so as to project outward from said distal end of said tubular body into the urinary bladder of the patient when said tubular body is in the urethra, said actuator rod supporting a first permanent magnet outside said lumen;

(e) a second permanent magnet when located exterior the patient's body proximate to said urinary incontinence valve, attracts said first permanent magnet to tip said actuator rod and said valve member relative to said valve seat surface, allowing urine flow through said annular valve seat surface of said lumen;

(f) a first foldable anchoring mechanism located on said distal end of said tubular body comprising a multi-lobed spring mechanism which when disposed in the bladder resists migration of the tubular body in the proximal direction; and (g) a second anchoring mechanism comprising a retaining spring selectively positionable proximate said urethra meatus for inhibiting migration of the tubular body in the distal direction in the urethra.

8. Urinary incontinence valve as in claim 7 and further including a compression spring disposed in said lumen for normally urging said generally planar valve member into sealing contact relative to said generally planar, annular valve seat surface with a predetermined force.

9. The urinary incontinence valve as in claim 8 wherein said compression spring is disposed proximal said valve surface.

10. A urinary incontinence valve of claim 7 wherein said multi-lobed umbrella spring mechanism is selectively movable between a first position extending generally transverse to a longitudinal axis of said tubular body and a second position generally parallel to said longitudinal axis of said tubular body.

11. A urinary incontinence valve of claim 7 wherein said second anchoring mechanism is selectively positionable with respect to said tubular body.

12. A urinary incontinence valve of claim 7 wherein said second anchoring mechanism is selectively removable from said tubular body.

13. A urinary incontinence valve of claim 7 and further including a tubular member surrounding said tubular body and folding the multi-lobed spring mechanism to said first position to facilitate insertion and removal of said incontinence valve.

* * * * *